United States Patent [19]
Li et al.

[11] Patent Number: 6,091,485
[45] Date of Patent: Jul. 18, 2000

[54] METHOD AND APPARATUS FOR OPTICALLY DETERMINING PHYSICAL PARAMETERS OF UNDERLAYERS

[75] Inventors: Guoguang Li; Hongwei Zhu, both of San Jose; Dale A. Harrison, Tracy; Abdul Rahim Forouhi, Cupertino; Weilu Xu, San Jose, all of Calif.

[73] Assignee: N & K Technology, Inc., Santa Clara, Calif.

[21] Appl. No.: 09/464,640

[22] Filed: Dec. 15, 1999

[51] Int. Cl.$^7$ .................................................. G01N 21/00
[52] U.S. Cl. ........................... 356/73; 356/382; 356/381; 250/559.28; 250/559.39
[58] Field of Search ............................. 356/73, 372, 381, 356/382, 357, 355; 250/559.28, 559.39

[56] References Cited

U.S. PATENT DOCUMENTS

| | | | |
|---|---|---|---|
| 3,601,492 | 8/1971 | Reichard | 356/108 |
| 4,355,903 | 10/1982 | Sandercock | 356/382 |
| 4,555,767 | 11/1985 | Case et al. | 364/563 |
| 4,676,647 | 6/1987 | Kikkawa et al. | 356/382 |
| 4,885,709 | 12/1989 | Edgar et al. | 364/563 |
| 4,899,055 | 2/1990 | Adams | 250/372 |
| 4,999,509 | 3/1991 | Wada et al. | 250/560 |
| 5,042,949 | 8/1991 | Greenberg et al. | 356/345 |
| 5,101,111 | 3/1992 | Kondo | 250/560 |
| 5,241,366 | 8/1993 | Bevis et al. | 356/382 |
| 5,311,284 | 5/1994 | Nishino | 356/364 |
| 5,337,150 | 8/1994 | Mumola | 356/382 |
| 5,365,340 | 11/1994 | Ledger | 356/357 |
| 5,371,596 | 12/1994 | Hattori et al. | 356/355 |
| 5,396,080 | 3/1995 | Hannotiau et al. | 250/560 |
| 5,457,534 | 10/1995 | Lacey et al. | 356/357 |
| 5,471,303 | 11/1995 | Ai et al. | 356/357 |
| 5,486,701 | 1/1996 | Norton et al. | 250/372 |
| 5,523,840 | 6/1996 | Nishizawa et al. | 356/355 |
| 5,541,733 | 7/1996 | Gagnon | 356/382 |
| 5,555,472 | 9/1996 | Clapis et al. | 356/357 |
| 5,747,813 | 5/1998 | Norton et al. | 250/372 |
| 5,784,167 | 7/1998 | Ho | 356/382 |
| 5,966,214 | 10/1999 | Imbrock et al. | 356/382 |

OTHER PUBLICATIONS

Li, G. et al., *A fast, easy way to measure the thickness of DLC films*, Data Storage, pp. 29–32, Jun. 1999.

*Primary Examiner*—Frank G. Font
*Assistant Examiner*—Roy M. Punnoose
*Attorney, Agent, or Firm*—Lumen Intellectual Property Services

[57] ABSTRACT

A method and apparatus for optically determining a physical parameter of an underlayer such as the underlayer refractive index $N_u$, extinction coefficient $k_u$ and/or thickness $t_u$ through a top layer having a first top layer thickness $t_1$ and an assigned refractive index index $n_t$ and coefficient of extinction $k_t$. The values of index $n_t$ and extinction coefficient $k_t$ can be estimated, optically determined or assigned based on prior knowledge. In a subsequent step a first reflectance $R_1$ is measured over a wavelength range $\Delta\lambda$ by using a test beam spanning that wavelength range. Then, a second reflectance $R_2$ of the top layer and underlayer is measured using the test beam spanning wavelength range $\Delta\lambda$ at a second top layer thickness $t_2$. In a calculation step the physical parameter of the underlayer is determined from the first reflectance measurement $R_1$, the second reflectance measurement $R_2$, and the assigned or predetermined thickness values $t_1$, $t_2$, and the refractive index $n_t$ and coefficient of extinction $k_t$ of the top layer. A dispersion model can be used in this calculation step. Alternatively, with transmissive samples, a first and second transmittance $T_1$, $T_2$ can be used.

25 Claims, 7 Drawing Sheets

METHOD AND APPARATUS FOR OPTICALLY DETERMINING PHYSICAL PARAMETERS OF UNDERLAYERS

FIELD OF THE INVENTION

This invention relates generally to methods and apparatus for optically determining physical parameters of underlayers, and in particular to the determination of physical parameters such as thickness, refraction index and extinction coefficient of underlayers.

BACKGROUND OF THE INVENTION

The determination of physical parameters of layers making up, e.g., a laminated or layered structure is very important, since many modern technologies use multi-layered materials for various functions. For example, in magnetic disks a thin magnetic underlayer deposited between a supporting substrate layer and a top protective layer (e.g., a diamond-like-carbon (DLC) layer) is used to store data. Precise characterization of the magnetic underlayer is essential to further advances in the field of magnetic storage. It is especially important to determine such physical parameters as thickness $t_u$, index of refraction $n_u$ and extinction coefficient $k_u$ of the magnetic underlayer. This presents considerable difficulty for many reasons. First, the underlayer is covered by the top layer and hence can not be measured directly by a non-destructive technique. Second, the magnetic underlayer, if exposed, will undergo oxidation and hence a direct measurements of its physical parameters will be flawed and will not reflect the actual physical parameters of the magnetic underlayer covered by the top layer. Third, the thickness of the top layers in this application as well as in many other applications where an underlayer is covered by a top layer is in the range of a few hundred Angstroms or even tens of Angstroms. In this range, typical optical measurements are not very reliable and hence the determination of physical parameters of the underlayer through such a thin top layer presents a challenge to optical methods.

Various prior art techniques exist for examining top thin films or layers. U.S. Pat. No. 3,601,492 to Reichert employs a standard interference technique for measuring film thickness based on observing the interference between the light reflected from the top and bottom surfaces of the thin film. Greenberg et al. teaches in U.S. Pat. No. 5,042,949 that film thickness can be determined by examining the interference pattern and reflectance data from a reflectance pattern, respectively to determine film thickness profile. Still another approach to determining thin film thickness is taught by Hattori et al. in U.S. Pat. No. 5,371,596. Here, the light from a light source is modulated to produce a modulated interference light. This modulated light is reflected from the thin film and used by a number of photodetectors to derive film thickness.

In U.S. Pat. No. 4,999,509 Wada et al. describe a how to measure thicknesses of several films using a reflectance measuring device.

Unfortunately, the above prior art approaches yield less and less satisfactory results for the thin film parameters with decreasing film thickness due to poor signal-to-noise ratios. Moreover, most of these techniques are for determining top films and are not easily adaptable to measuring the physical properties of underlayers.

There are various other prior art approaches to measuring thin film thickness and other physical parameters. However, most of these are complicated and not capable of providing the desired levels of accuracy. Moreover, none of the prior art techniques can be adapted for high-precision measurements of sandwiched films or underlayers.

Hence, there is a pressing need to develop an approach which will enable one to measure the thickness as well as other physical properties of underlayers to a high degree of accuracy. This is particularly important when non-destructive measurement of the underlayer is required and/or the underlayer changes its properties when examined directly, i.e., without the protection afforded by a top layer. It would be very desirable to provide a non-destructive measurement method for determining underlayer thickness to a high level of accuracy. It would also be desirable if such underlayer measurement could provide further information about the top layer.

OBJECTS AND ADVANTAGES OF THE INVENTION

Accordingly, it is a primary object of the present invention to provide a method and an apparatus for optically determining physical parameters of underlayers. In particular, the apparatus and method should enable one to determine the refraction and extinction coefficients $n_u$ and $k_u$ to a high degree of accuracy and also yield accurate values of other physical parameters including thickness $t_u$ in cases where the underlayer is not opaque.

It is another object of the invention to enable one to evaluate the above physical parameters of underlayers in a non-destructive manner. Additionally, the method of the invention should be easy to employ in practical situations.

It is a further object of the invention to measure the physical parameters of the underlayer in a manner which provides further information about the top layer.

The above objects and advantages, as well as numerous other improvements attained by the method and apparatus of the invention are pointed out below.

SUMMARY

The objects and advantages of the invention are achieved by a method for optically determining a physical parameter of an underlayer such as the underlayer refractive index $n_u$, extinction coefficient $k_u$ and/or thickness $t_u$. The method calls for providing a transparent top layer having a first top layer thickness $t_1$ on the underlayer and assigning a refractive index index $n_t$ and a coefficient of extinction $k_t$ to the top layer. The values of index $n_t$ and extinction coefficient $k_t$ can be estimated, optically determined or assigned based on prior knowledge. In a subsequent step a first reflectance $R_1$ is measured over a wavelength range $\Delta\lambda$ by using a test beam spanning that wavelength range. The first reflectance $R_1$ is made up of a first reflectance response of the top layer at thickness $t_1$ and a first reflectance response of the underlayer. Additional background response can also be present.

A second reflectance $R_2$ of the top layer and underlayer is measured using the test beam spanning wavelength range $\Delta\lambda$ at a second top layer thickness $t_2$. For example, the thickness of the top layer can be changed, e.g., by depositing additional material. In this case second thickness $t_2$ is larger than first thickness $t_1$. Of course, one can also abrade the top layer from a larger thickness $t_1$ to a lesser thickness $t_2$. Alternatively, a first region of the top layer can have thickness $t_1$ while a second region has thickness $t_2$. In the latter case, second reflectance $R_2$ is simply measured in the second region of the top layer. Preferably, first top layer thickness $t_1$ and second top layer thickness $t_2$ are selected to maximize a reflectance difference between said first reflectance $R_1$ and said second reflectance $R_2$.

The second reflectance $R_2$ has a second reflectance response of the top layer at second top layer thickness $t_2$ and a second reflectance response of the underlayer. As before, additional background response can also be present.

In a calculation step the physical parameter of the underlayer is determined from the first reflectance measurement $R_1$, the second reflectance measurement $R_2$, and the assigned or predetermined thickness values $t_1$, $t_2$, the refractive index $n_t$ and coefficient of extinction $k_t$ of the top layer. A dispersion model can be used in this calculation step.

In a preferred embodiment the refractive index $n_u$, extinction coefficient $k_u$ and thickness $t_u$ of the underlayer are determined and the method further allows one to calculate an unknown top layer thickness $t_x$ e.g., in a different sample. This is possible in the case where the assignment of refractive index index $n_t$ and of coefficient of extinction $k_t$ of the top layer is based on actually determined values, e.g., optically determined values or a priori known values or when these values are estimated, and when $t_1$, $t_2$ are also known a priori.

The method of the invention is non-destructive and is particularly useful when the underlayer is made of or contains an environmentally degradable material; e.g., when the underlayer contains an oxidizable material. In this case the top layer is preferably a protective layer which shields the underlayer from the degrading effects of the ambient environment.

The underlayer is usually deposited on a substrate. In this case the first reflectance $R_1$ and the second reflectance $R_2$ can include a first and second reflectance response of the substrate respectively. This is the case when the underlayer is transmissive to at least a portion of wavelength range $\Delta\lambda$ contained in the test beam.

An apparatus of the invention optically determines a physical parameter of the underlayer with the aid of a light source generating a test beam in wavelength range $\Delta\lambda$ for illuminating the underlayer and the top layer at first and second top layer thicknesses $t_1$, $t_2$. The first and second reflectances $R_1$, $R_2$ are measured by a detector which is connected to a computing unit. The computing unit calculates the physical parameter of the underlayer from first and second reflectances $R_1$, $R_2$, refractive index $n_t$ and coefficient of extinction $k_t$.

The method and apparatus of the invention can be used in situation when the underlayer should not be exposed to the ambient environment and the determination is to be made in a non-destructive manner. For example, the method and apparatus of the invention are used in determining physical parameters of underlayers consisting of magnetic materials (e.g., such as used in magnetic recording media) as well as elemental metals and alloys of such. Specifically in the case of magnetic media, the top layer can be a protective layer made of diamond-like carbon or a different carbon structure. Of course, other protective layers such as silicon oxide, aluminum oxide, silicon carbide can also constitute the top layer in other layered structures.

The invention can also be based on transmission measurements performed at first and second top layer thicknesses. This is possible when the top layer and underlayer as well as any eventual substrate are transmissive over wavelength range $\Delta\lambda$.

A detailed description of the invention and the preferred and alternative embodiments is presented below in reference to the attached drawing figures.

DETAILED DESCRIPTION

Figure 1:
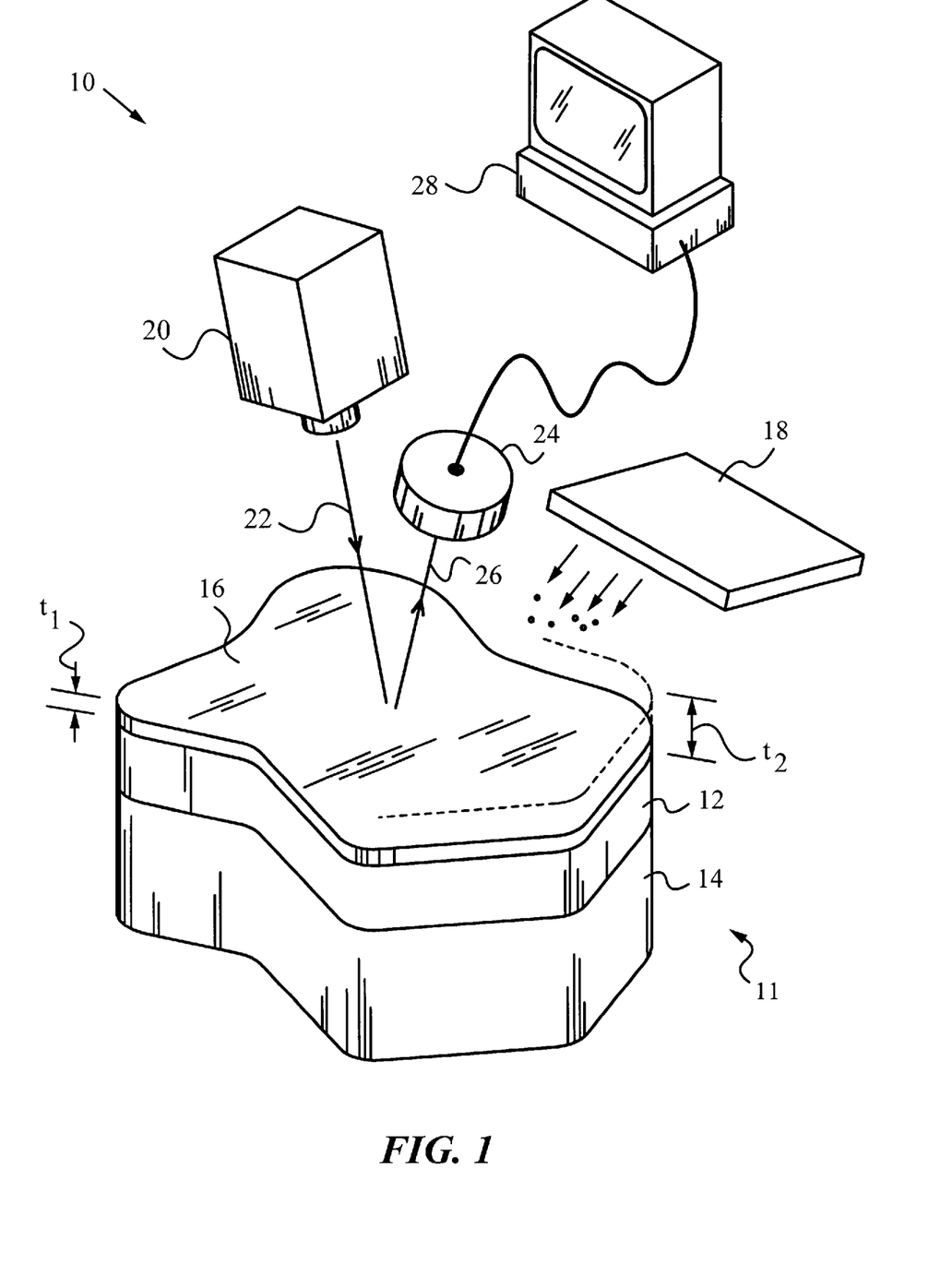
FIG. 1 is an isometric view of an apparatus for performing a first and second reflectance $R_1$, $R_2$ measurements in accordance with the invention.

FIG. 1 illustrates an apparatus 10 in accordance with the invention for performing optical measurements of a sample 11 composed of a substrate 14, an underlayer 12 deposited on substrate 14, and a top layer 16 covering underlayer 12. Specifically, apparatus 10 is used to measure physical parameters of underlayer 12. Underlayer 12 can be made of an environmentally degradable material which becomes degraded, e.g., by oxidation with atmospheric oxygen and hence requires top layer 16 for protection. Underlayer 12 can also be made of a material which is not degradable. In either case, top layer 16 can be a protective layer.

Top layer 16 has a first thickness $t_1$ of preferably less than 100 Å and possibly in the range of a few tens of Å or even less. Alternatively, top layer 16 can also be thicker as long as it is transparent. It is deposited with a suitable depositing device 18 such as a sputtering apparatus or a coating device. In fact, it is preferable that device 18 be also capable of depositing underlayer 12 on substrate 14 before deposition of top layer 16. A person of average skill in the art will select the most suitable device 18 in accordance with the requirements and the material of top layer 16.

As indicated in dashed lines, top layer 16 is later augmented by deposition to a second thickness $t_2$, which preferably remains in the same thickness range as $t_1$, but can also be significantly larger. Of course, the second measurement could also be performed on another sample built up the same way as sample 11 but with top layer 16 having second thickness $t_2$. In case top layer 16 serves as protective layer for underlayer 12, thickness $t_2$ can be the final desired thickness as required for the fulfillment of layer's 16 protective functions.

Apparatus 10 has a light source 20 for delivering a test beam 22. Light source 20 can be a tunable laser or any other suitable light source or combination of light sources for producing stable light spanning a wavelength range $\Delta\lambda$, e.g., from 190 nm to 900 nm. The top layer 16 is made of a material which is transparent to light in wavelength range $\Delta\lambda$. Light source 20 is oriented such that beam 22 illuminates or is incident on top layer 16 and propagates into underlayer 12 at a near-normal angle of incidence. In principle, however, the angle of incidence can have any value.

A detector 24 is positioned to receive a reflected light beam 26. Detector 24 is a charge-coupled device (CCD), a diode array or any other suitable light detector which can reliably measure light intensity over wavelength range $\Delta\lambda$. Detector 24 is connected to a computing unit 28 capable of analyzing the reflectance data from the measurements of sample 11 at the two thicknesses $t_1$, $t_2$ and any reference or baseline samples which may be measured for comparison or calibration. Although in this embodiment computing unit 28 is represented by a personal computer, any suitable signal processing and computing device can be employed, as will be appreciated by those skilled in the art.

The spectral composition or spectrum of reflected beam 26 will vary depending on the reflectance of sample 11. The reflectance data from sample 11 is used to determine the physical parameters of underlayer 12.

Figure 2A:
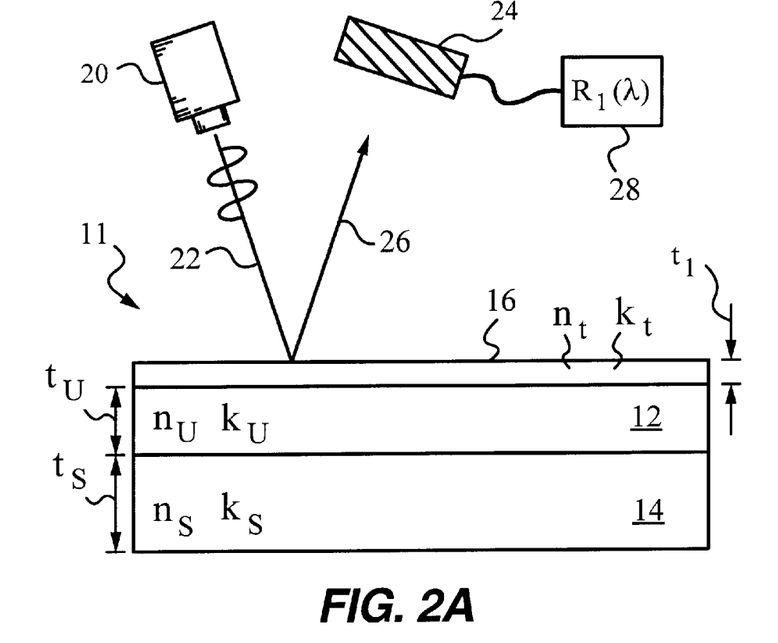
FIG. 2A is a cross sectional view showing an underlayer on a substrate with a top layer at first thickness $t_1$ set up for measurement according to the invention.

Referring now to the cross sectional view of FIG. 2A, a first reflectance $R_1$ ($R_1(\lambda)$) of sample 11 over wavelength range $\Delta\lambda$ at first thickness $t_1$ of top layer 16 is obtained from reflected beam 26 by detector 24. Reflectance $R_1$ signal is made up of a first reflectance response of top layer 16 at first thickness $t_1$ and a first reflectance response of underlayer 12. Additional background reflectance response or contribution can also be present in first reflectance $R_1$ spectrum. This background reflectance can include a first reflectance response of substrate 14 in the event underlayer 12 is transparent over a portion of or over the entire wavelength range $\Delta\lambda$ of beam 22.

Figure 2B:
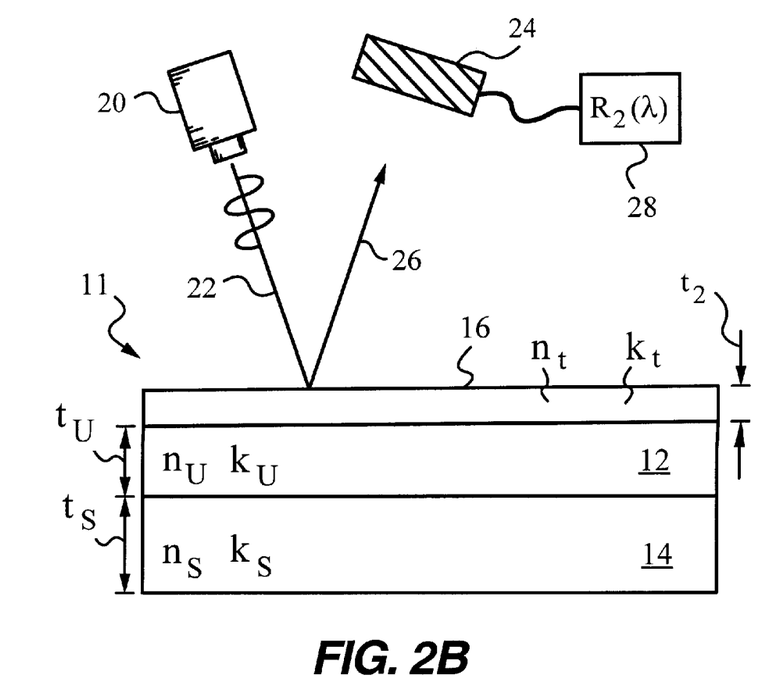
FIG. 2B is a cross sectional view showing the structure of FIG. 2A with the top layer at second thickness $t_2$ set up for measurement according to the invention.

FIG. 2B illustrates the measurement of a second reflectance $R_2$ ($R_2(\lambda)$) over wavelength range $\Delta\lambda$ at second thickness $t_2$ of top layer 16. Once again, the reflectance data is obtained from reflected beam 26 by detector 24. Reflectance $R_2$ signal is made up of a second reflectance response of top layer 16 at second thickness $t_2$ and a second reflectance response of underlayer 12. The background contribution can include a second reflectance response of substrate 14 as is the case in reflectance $R_1$ signal.

The calculation of physical parameters of underlayer 12 from reflectance data is performed by computing unit 28. For example, the physical parameters of underlayer 12 which can be determined are underlayer thickness $t_u$, index of refraction $n_u$ and extinction coefficient $k_u$. A person of average skill in the art will recognize that other physical parameters such as badgap energy $E_g$ and structural constants of underlayer 12 can also be determined from reflectance data in accordance with known techniques. For simplicity, only determination of underlayer thickness $t_u$, index of refraction $n_u$ and extinction coefficient $k_u$ will be discussed herein.

To determine physical parameters $t_u$, $n_u$ and $k_u$ unit 28 uses first reflectance $R_1(\lambda)$ and second reflectance $R_2(\lambda)$ data as measured. In addition, computing unit 28 uses in its determination several physical parameters of top layer 16. These top layer 16 parameters include thicknesses $t_1$, $t_2$ and the values of index of refraction $n_t$ and extinction coefficient $k_t$. The values for top layer 16 index $n_t$ and coefficient $k_t$ are assigned values. These values can be based on prior knowledge, e.g., they can be obtained from standard tables, or they can be estimated. Preferably, $n_t$ and $k_t$ are measured, e.g., determined by optical or other methods.

There are several models for measuring thicknesses $t_1$, $t_2$ as well as coefficients $n_t$ and $k_t$ of top layer 16 based on how these physical parameters affect the reflectance spectrum in beam 26. A particularly useful prior art model for determining the physical parameters of top layer 16 is the Forouhi-Bloomer technique described in U.S. Pat. No. 4,905,170 which is herein incorporated by reference. This technique is based on the following equations:

$$k(E) = \sum_{i=1}^{q} \frac{A_i(E - E_g)^2}{E^2 + B_i E + C_i},$$

$$n(E) = n(\infty) + \sum_{i=1}^{q} \frac{B_{0i} E + C_{0i}}{E^2 + B_i E + C_i}.$$

In these equations E is the photon energy, which is related to wavelength $\lambda$ according to $E = hc/\lambda$, where h is Planck's constant and c is the speed of light in vacuum. $E_g$ is the bandgap energy or the minimum photon energy required for absorption, and A, B and C are parameters directly related to the electronic structure of the material of top layer 16. The term $n(\infty)$ represents the value of index $n(\lambda)$ as $\lambda$ tends toward infinity. The quantities $B_0$ and $C_0$ are not independent parameters but depend on A, B, C and $E_g$. The equation for $n(E)$ is derived from the equation for $k(E)$ through the well-known Kramers-Kronig dispersion relation.

The Forouhi-Bloomer model incorporates the above equations into the Fresnel coefficients, along with a factor that depends on interface roughness a between top layer 16 and underlayer 12 to generate a calculated or theoretical reflectance spectrum, $R_{th}$ of sample 11 with top layer 16 at first thickness $t_1$ and then at second thickness $t_2$. The quantity $R_{th}$ is then compared to the experimentally measured reflectance spectrum, R of sample 11 with top layer 16 over wavelength range $\Delta\lambda$. Specifically, the comparisons are made between $R_{th}$, R obtained at $t_1$ and $R_{th}$, R obtained at $t_2$. This comparison can be advantageously performed with the aid of a non-linear least-squares fit:

$$\delta = \sqrt{\frac{1}{N} \sum_{i=1}^{N} [R(\lambda_i) - R_{th}(\lambda_i)]^2}.$$

Typically, wavelength range $\Delta\lambda$ is selected from 190 nm to 900 nm in 1 nm intervals; thus, N=711. To obtain the values of the physical parameters of film 16, the quantities involving these physical parameters, specifically first thickness $t_1$, roughness $\sigma$, A, B, C, n $(\infty)$ and Eg are varied such that $\delta$ is minimized. This minimization is complete after several iterations. The final parameters then yield the physical parameters including $t_1$, $n_t(\lambda)$, $k_t(\lambda)$, $\sigma$ and $E_g$. The same process is repeated at second thickness $t_2$ to obtain the actual value of $t_2$.

It should be noted, that top layer 16 does not have to be measured on top of underlayer 12. For example, top layer 16 can be deposited on another substrate, e.g., silicon or silicon 1o oxide, to the same thicknesses $t_1$, $t_2$ and examined thereon.

From the values of $t_1$, $t_2$, $n_t$, $k_t$ of top layer 16 and first and second reflectances $R_1$, $R_2$ unit 28 determines $t_u$, $n_u$ and $k_u$ of underlayer 12. For most accurate determination of $t_u$, $n_u$ and $k_u$ it is preferred that first reflectance $R_1$ signal differ significantly from second reflectance $R_2$ signal over wavelength range $\Delta\lambda$. This can be accomplished by selecting the physical parameters, i.e., the material, and thicknesses $t_1$, $t_2$ of top layer 16 to get an easily measurable difference $\Delta R$ between reflectances $R_1$ and $R_2$. Preferably, the difference $\Delta R$ should be maximized to the extent possible while not experiencing excessive signal loss from underlayer 12. This can be best accomplished when top layer 16 is transparent over $\Delta\lambda$, since this gives one a wide latitude in the selection of thicknesses $t_1$ and $t_2$. In some cases the user will have no control over the material of top layer 16 and the only physical parameters which he or she will be able to choose are thicknesses $t_1$, $t_2$. In cases where the user has a choice of material of top layer 16 as well as thicknesses $t_1$, $t_2$ both the selection of the material and thicknesses $t_1$, $t_2$ is done such as to obtain a sufficiently large reflectance difference $\Delta R$.

Of course, any optical models, including dispersive models such as the Forouhi-Bloomer model discussed above can be used by unit 28 in computing $n_u$ and $k_u$ of underlayer 12. It should be noted that thickness $t_u$ of underlayer 12 can be measured when underlayer 12 is transmissive. Again, any optical models can be used in determining $t_u$.

The method and apparatus 10 of the invention are particularly useful in situations when underlayer 12 should not or can not be exposed to the ambient environment and the determination is to be made in a non-destructive manner. For example, this is the case when underlayer 12 is a magnetic material such as a magnetic alloy (also referred to as Mag layer) or a layer made of an elemental metal or an alloy of an elemental metal. In the case of Mag underlayer 12 top layer 16 can be a protective layer made of diamon-like carbon. Of course, other protective layers such as silicon oxide, aluminum oxide, silicon carbide and others can also constitute top layer 16 in this and other layered structures.

Figure 5:
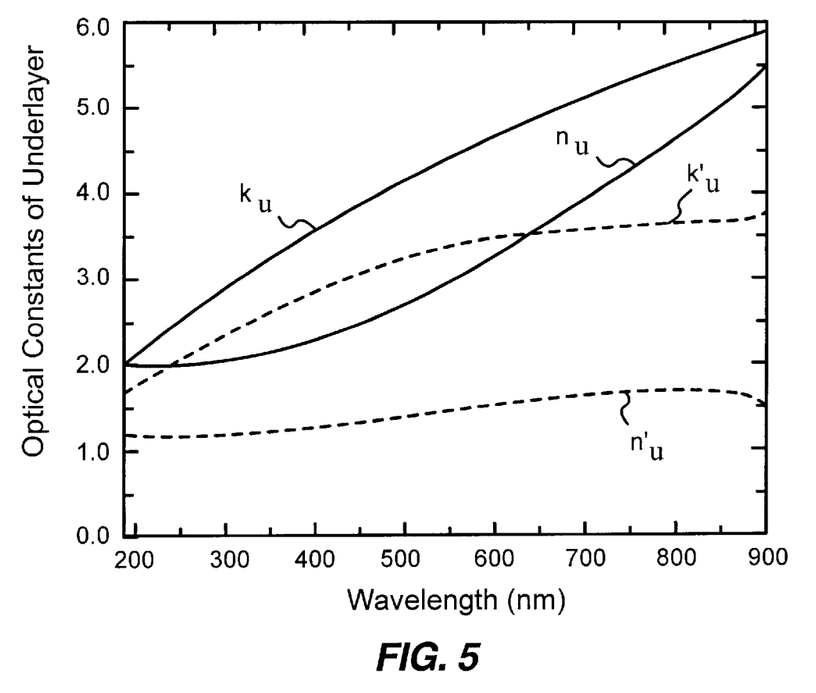
FIG. 5 are graphs of correct underlayer parameters $k_u$, $n_u$ obtained with correct parameters $k_t$, $n_t$, $t_u$ and graphs of incorrect underlayer parameters $k_u'$, $n_u'$, $t_u'$ obtained with incorrect top layer parameters $k_t'$, $n_t'$.

The performance of the method of the invention in determining $n_u$ and $k_u$ of a non-transparent underlayer 12 is illustrated in the graphs of FIG. 5. In this example underlayer 12 is a Mag underlayer deposited on a typical substrate 14 used in magnetic recording media Cr/NiP/Al. Top layer 16 is a protective DLC layer with first thickness $t_1$=49 Å and second thickness $t_2$=118 Å.

The thickness of Mag underlayer 12 is 280 Å, the thickness of Cr is 400 Å, the thickness of NiP is 8 $\mu$m and the thickness of Al is on the order of several mm. Since Mag underlayer 12 is almost opaque its thickness $t_u$ can not be accurately measured by optical methods.

Figure 4A:
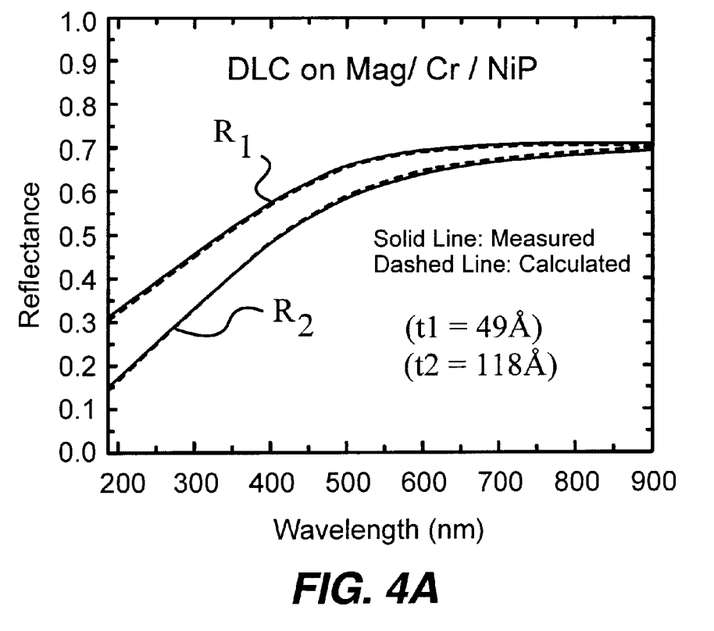
FIG. 4A are graphs of measured and calculated reflectances $R_1$, $R_2$ for the same underlayer of magnetic material on Cr/NiP as in FIG. 3 at two thicknesses $t_1$=49 Å and $t_2$=118 Å of a top layer made of diamond-like carbon (DLC).
Figure 4B:
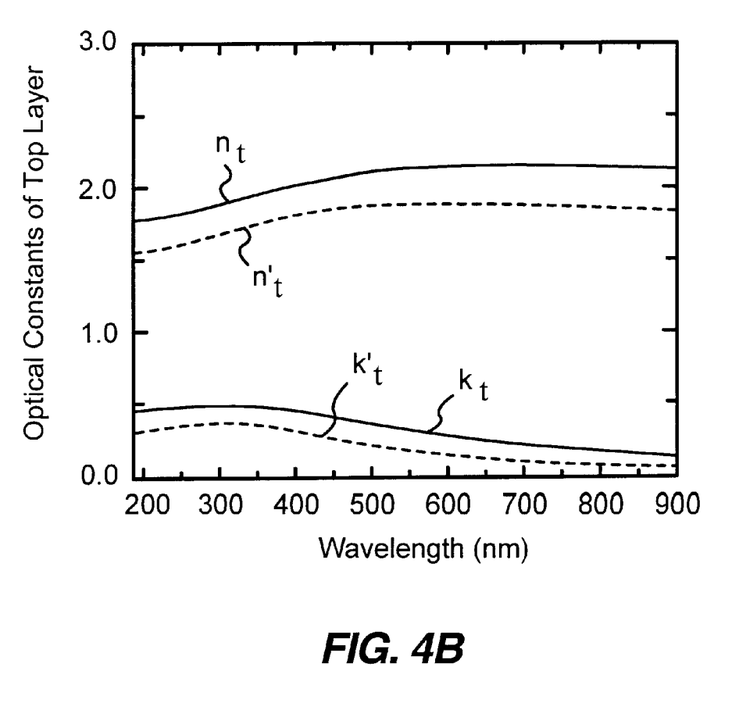
FIG. 4B are graphs of correct top layer parameters $k_t$, $n_t$ and incorrect top layer parameters $k_t'$, $n_t'$.

By measuring with top layer 16 protecting Mag underlayer 12 the method of the invention overcomes the above problem. The graphs in FIG. 4A illustrate reflectances $R_1$, $R_2$ as measured (solid lines) and as calculated (dashed lines) using correct values of $n_t$ and $k_t$. Clearly, the calculated and measured results are in excellent agreement. Hence, underlayer 12 parameters $n_u$ and $k_u$ obtained from the measured reflectances $R_1$, $R_2$ and graphed in FIG. 5 in solid lines are very accurate. In particular, the solid graphs of FIG. 5 were generated by fitting reflectances $R_1$, $R_2$ simultaneously using the Forouhi-Bloomer method with assigned values of $t_1$=49 Å, $t_2$=118 Å, and correct $n_t$ and $k_t$ for DLC layer 16 as illustrated in solid lines in the graphs of FIG. 4B. In this case, of $n_t$ and $k_t$ were obtained from a prior optical measurement of top layer also using the Forouhi-Bloomer method.

Figure 3:
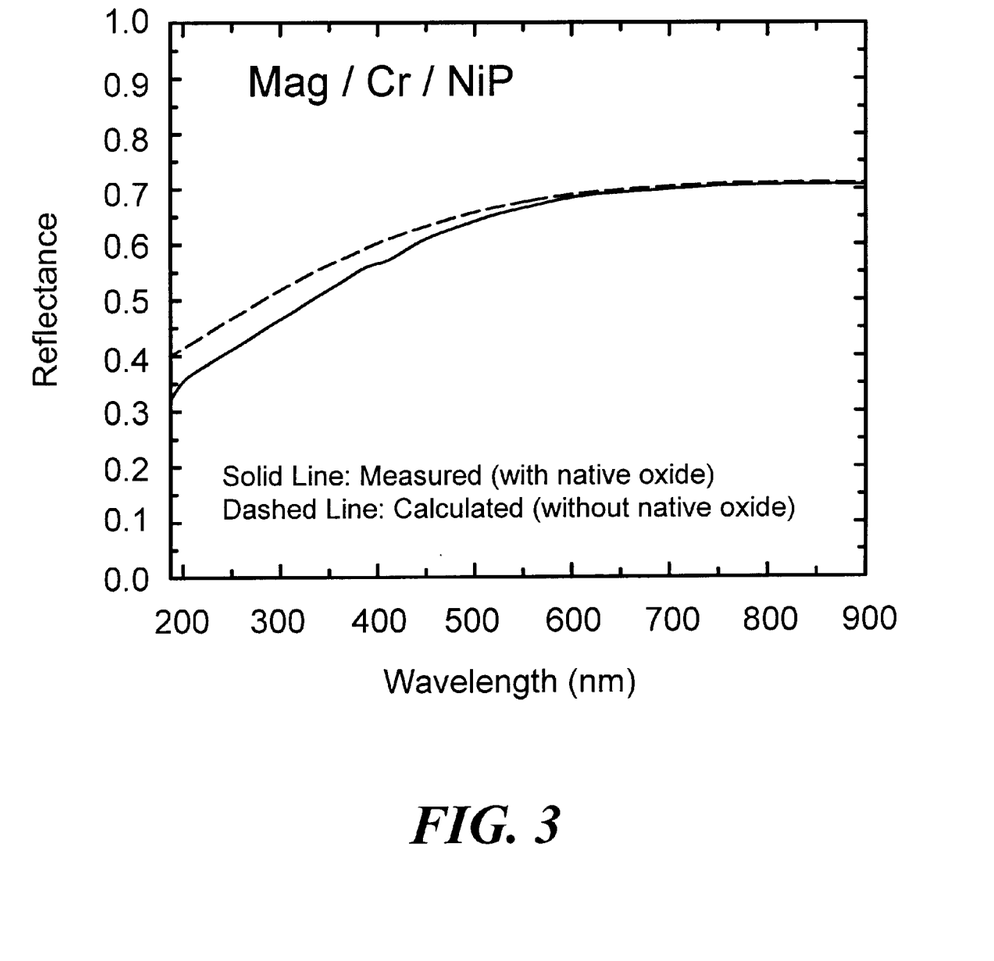
FIG. 3 are graphs of calculated reflectance (unexposed or without oxide layer) and measured reflectance (exposed or with oxide layer) performed on an unprotected underlayer made of a magnetic material and deposited on a Cr/NiP substrate.

For comparison purposes, FIG. 3 shows a graph of the measured (with native oxide) and calculated (without native oxide) reflectance of Mag underlayer 12 not protected by top layer 16 (i.e., Mag underlayer 12 is in fact the topmost layer in this case). The Mag material oxidizes rapidly when exposed to the atmosphere. The "native" oxide layer that forms on top of the Mag affects the "apparent" characteristics of Mag underlayer 12 and thus degrades the accuracy of optical measurement, because the actual underlayer 12 will not be oxidized. Thus, the measured reflectance over wavelength range $\Delta\lambda$ from 190 to 900 nm deviates significantly from the calculated reflectance. The problem is especially acute at shorter wavelengths where the oxide exhibits a strong influence. This inaccuracy in the measured reflectance makes it impossible for prior art methods to obtain accurate values of $n_u$ and $k_u$ in their measurements.

Alternatively, parameters $n_t$ and $k_t$ could be assigned or estimated and they may be incorrect. The method of the invention has the advantage that even if incorrect top layer parameters $n_t'$ $k_t'$ (primes indicating incorrect parameters) are used, an unknown top layer thickness $t_x$, e.g., in a similar sample 11, can still be correctly determined. In this case, however, first thickness $t_1$ and second thickness $t_2$ of top layer 16 have to be known. In addition, it is preferable that the difference between first and second thicknesses $t_1$ and $t_2$ be large and span a significant portion of the range within which the unknown thickness $t_x$ is measured.

Figure 6:
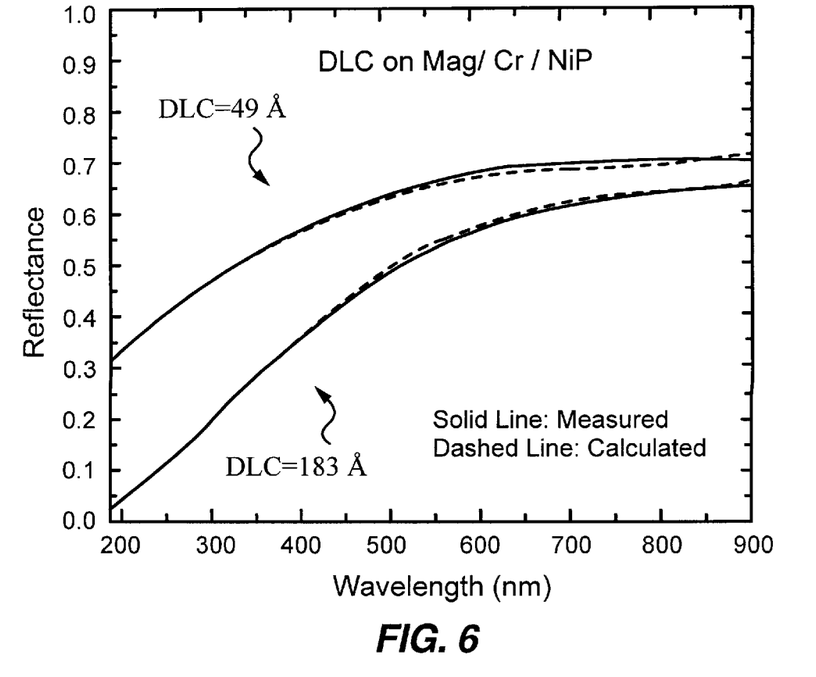
FIG. 6 are graphs of measured and calculated reflectances $R_1$, $R_2$ of for a sample with a DLC top layer at two thicknesses $t_1$=49 Å and $t_2$=183 Å.

To illustrate, FIG. 6 shows the measured (solid lines) and calculated (dashed lines) reflectances $R_1$, $R_2$ for another sample 11 with a DLC top layer 16 having top layer thicknesses $t_1$=49 Å and $t_2$=183 Å. The calculated reflectances $R_1$, $R_2$ used correct values of thicknesses $t_1$=49 Å and $t_2$=183 Å, but incorrectly assigned top layer parameters $n_t'$ $k_t'$ as shown in dashed lines in the graphs of FIG. 4B and incorrect thickness $t_u'$=350 Å of Mag underlayer 12 (rather than correct thickness $t_u$=280 Å). Still, reflectances $R_1$, $R_2$ calculated and measured are very close. The result of using these incorrect values results in incorrect parameters $n_u'$, $k_u'$ (incorrect indicated by primes) of underlayer 12 as indicated in dashed lines in FIG. 5.

Although the thickness $t_u$ of Mag underlayer 12 could not be measured in this case, the method of invention can also be used to determine $t_u$ where the underlayer is transparent, as indicated above.

Figure 7:
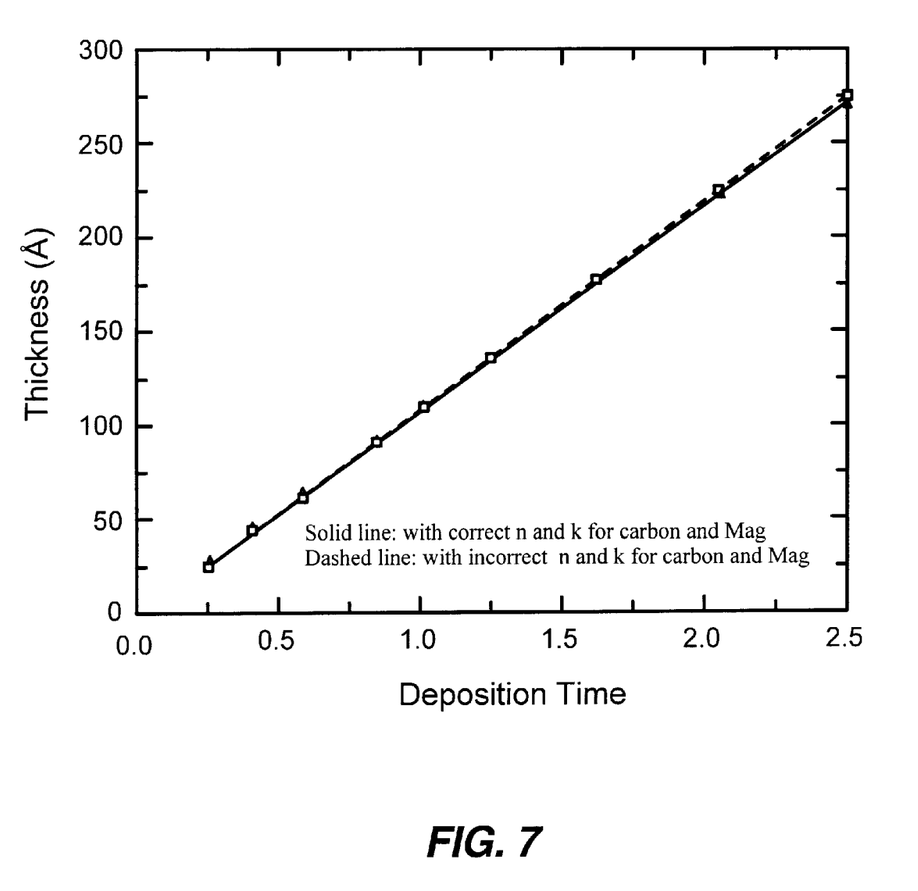
FIG. 7 are graphs comparing the performance of the method of the invention in determining an unknown top layer thickness $t_x$ from incorrect parameters of top layer and underlayer and the correct parameters.

FIG. 7 illustrates how the use of incorrect $k_t'$, $n_t'$ as well as incorrect $k_u'$, $n_u'$ and thickness $t_u'$ in the computations versus correct parameters $k_t$, $n_t$, $k_u$, $n_u$, and $t_u$ affects the determination of an unknown top layer 16 thickness $t_x$. Preferably, the Forouhi-Bloomer method is employed to determine $t_x$. The graphs of $t_x$ obtained with the correct and incorrect parameters are very close over a long range of deposition time. Thus, the incorrect parameters can clearly be used in determining unknown top layer 16 thickness $t_x$. One will observe that once thickness $t_x$ is well outside the range between $t_1$ and $t_2$, the thickness $t_x$ obtained with the incorrect parameters becomes less accurate. It should also be noted that in the event parameters $n_t$, $k_t$ are incorrect estimates ($n_t'$, $k_t'$) and thicknesses $t_1$, $t_2$ are also incorrect estimates ($t_1'$, $t_2'$) then $t_x$ in similar sample 11 can only be determined relative to $t_1$, $t_2$.

There are numerous modifications to the method of the invention which will be apparent to a person of average skill in the art. For example, the method of the invention can use polarized test beams or study a certain polarization of the reflected beam 26 in determining reflectances $R_1$, $R_2$. Such ellipsometric techniques require the use of analyzers (polarizers) which are well-known in the art. In addition, various phase and intensity data of reflected beam 26 can also be studied.

Figure 8:
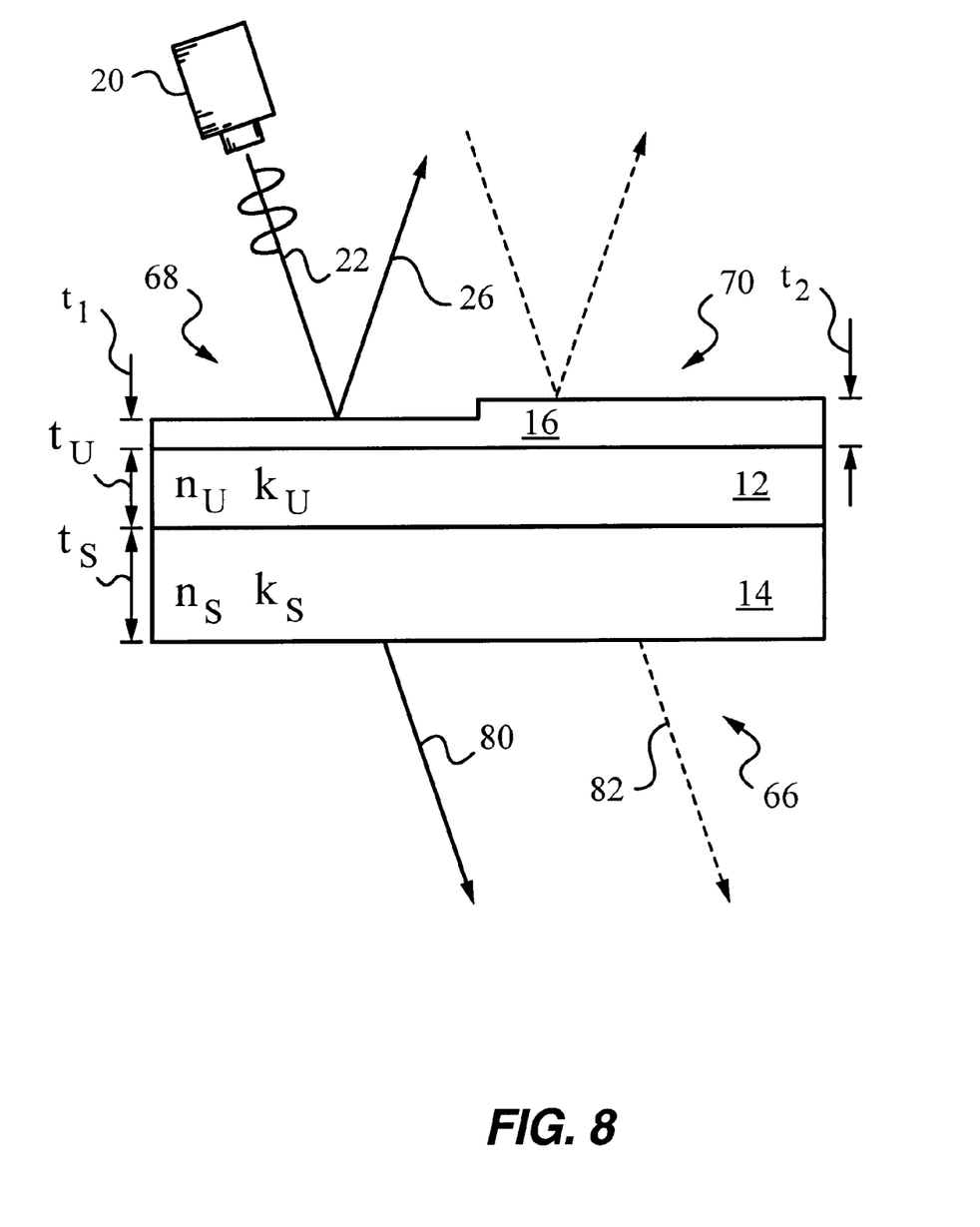
FIG. 8 is a cross sectional view illustrating another embodiment of the invention.

Although in the above embodiments first thickness $t_1$ is smaller than second thickness $t_2$, the situation can be reversed. For example, $t_1$ can be a larger thickness. After measuring reflectance $R_1$ sample 11 can be machined, e.g., polished or abraded to thickness $t_2$. In this case $t_2$ can also be the final thickness. In yet another embodiment, as shown in FIG. 8, a sample 66 can have two regions 68, 70 of thickness $t_1$ and $t_2$ respectively. The measurement of reflectances $R_1$, $R_2$ can thus be performed without an intervening deposition or abrasion. Neither $t_1$ nor $t_2$ have to be the final thickness top layer 16.

Of course, measurements of reflectance can also be performed at more than two thicknesses of the top layer. Also, $t_1$ and $t_2$ can be the minimum and maximum thicknesses of the top layer or two intermediate thicknesses. In some cases this will yield more reliable measurement data and hence more accurate values of the physical parameters of the underlayer, or thicknesses of the top layer.

In yet another embodiment, if sample 11 is composed of transmissive layers, i.e., top layer 16, underlayer 12 and eventual substrate 14 are transmissive over wavelength $\Delta\lambda$, then the above measurements can be based on sample 11 transmission measurements. In particular, in this embodiment, as indicated in FIG. 8, two transmission measurements $T_1$, $T_2$ are performed using transmitted beams 80, 82 at first top layer 16 thickness $t_1$ and second top layer 16 thickness $t_2$ respectively. Once again, preferably the Forouhi-Bloomer method is used in determining underlayer 12 parameters based on these transmission measurements.

It will be clear to one skilled in the art that the above embodiment may be altered in many ways without departing from the scope of the invention. Accordingly, the scope of the invention should be determined by the following claims and their legal equivalents.

What is claimed is:

1. A method for optically determining a physical parameter of an underlayer, said method comprising the following steps:
   a) providing on said underlayer a top layer at a first top layer thickness $t_1$;
   b) assigning a refractive index $n_t$ and a coefficient of extinction $k_t$ to said top layer;
   c) measuring a first total optical response $O_1$ over a wavelength range $\Delta\lambda$ by using a test beam having said wavelength range $\Delta\lambda$, said first total optical response $O_1$ comprising a first optical response of said top layer at said first top layer thickness $t_1$ and a first optical response of said underlayer;
   d) providing on said underlayer said top layer at a second top layer thickness $t_2$;
   e) measuring a second total optical response $O_2$ over said wavelength range $\Delta\lambda$ using said test beam, said second total optical response $O_2$ comprising a second optical response of said top layer at said second top layer thickness $t_2$ and a second optical response of said underlayer; and
   f) calculating said physical parameter from said first total optical response $O_1$, said second total optical response $O_2$, said refractive index $n_t$, said coefficient of extinction $k_t$, said first top layer thickness $t_1$ and said second top layer thickness $t_2$.

2. The method of claim 1, wherein said assignment of said refractive index $n_t$ and said coefficient of extinction $k_t$ comprises an estimation.

3. The method of claim 2, wherein said physical parameter of said underlayer is selected from the group consisting of refractive index $n_u$, extinction coefficient $k_u$ and thickness $t_u$.

4. The method of claim 3, wherein refractive index $n_u$, extinction coefficient $k_u$, and thickness $t_u$ of said underlayer are determined and said method further comprises calculating an unknown thickness $t_x$ of said top layer.

5. The method of claim 2, wherein said calculating step comprises a calculation using a dispersion model.

6. The method of claim 1, wherein said assignment of said refractive index $n_t$ and said coefficient of extinction $k_t$ comprises an optical determination.

7. The method of claim 6, wherein said physical parameter of said underlayer is selected from the group consisting of refractive index $n_u$, extinction coefficient $k_u$ and thickness $t_u$.

8. The method of claim 7, wherein refractive index $n_u$, extinction coefficient $k_u$ and thickness $t_u$ of said underlayer are determined and said method further comprises calculating an unknown thickness $t_x$ of said top layer.

9. The method of claim 6, wherein said calculating step comprises a calculation using a dispersion model.

10. The method of claim 1, wherein said underlayer comprises an environmentally degradable material.

11. The method of claim 10, wherein said underlayer comprises an oxidizable material.

12. The method of claim 1, wherein said top layer is a protective layer.

13. The method of claim 1, wherein said underlayer is deposited on a substrate.

14. The method of claim 13, wherein said first total optical response $O_1$ and said second total optical response $O_2$ further comprise a first and second optical response of said substrate respectively.

15. The method of claim 1, wherein said second top layer thickness $t_2$ is larger than said first top layer thickness $t_1$.

16. The method of claim 1, wherein estimates of said top layer refractive index $n_t$ and extinction coefficient $k_t$ are assigned in said assigning step.

17. The method of claim 1, wherein said first total optical response $O_1$ is a first total reflectance $R_1$ and said second total optical response $O_2$ is a second total reflectance $R_2$.

18. The method of claim 1, wherein said first total optical response $O_1$ is a first total transmittance $T_1$ and said second total optical response $O_2$ is a second total transmittance $T_2$.

19. An apparatus for optically determining a physical parameter of an underlayer covered by a top layer having a first top layer thickness $t_1$, a second top layer thickness $t_2$, an assigned refractive index $n_t$ and an assigned coefficient of extinction $k_t$, said apparatus comprising:
   a) a light source for illuminating said underlayer and said top layer at said first top layer thickness $t_1$ and at said second top layer thickness $t_2$ with a test beam comprising a wavelength range $\Delta\lambda$;
   b) a detector for measuring a first total optical response $O_1$ and a second total optical response $O_2$ over said wavelength range $\Delta\lambda$, said first total optical response $0_1$ comprising a first optical response of said top layer at said first top layer thickness $t_1$ and a first optical response of said underlayer, said second total optical response $O_2$ comprising a second optical response of said top layer at said top layer thickness $t_2$ and a second optical response of said underlayer; and
   c) a computing unit in communication with said detector for determining said physical parameter from said first total optical response $O_1$, said second total optical response $O_2$, said refractive index $n_r$ and said coefficient of extinction $k_r$, said first top layer thickness $t_1$ and said second top layer thickness $t_2$.

20. The apparatus of claim 19, wherein said top layer has a first region at said first top layer thickness $t_1$ and a second region at said second top layer thickness $t_2$.

21. The apparatus of claim 19, wherein said underlayer comprises an environmentally degradable material.

22. The apparatus of claim 21, wherein said underlayer comprises an oxidizable material.

23. The apparatus of claim 21, wherein said underlayer comprises a material selected from the group consisting of magnetic materials, elemental metals, and alloys of elemental metals.

24. The apparatus of claim 19, wherein said top layer is a protective layer.

25. The apparatus of claim 24, wherein said top layer comprises a material selected from the group consisting of diamond-like carbon, silicon oxide, aluminum oxide and silicon carbide.

* * * * *